Figure 1:
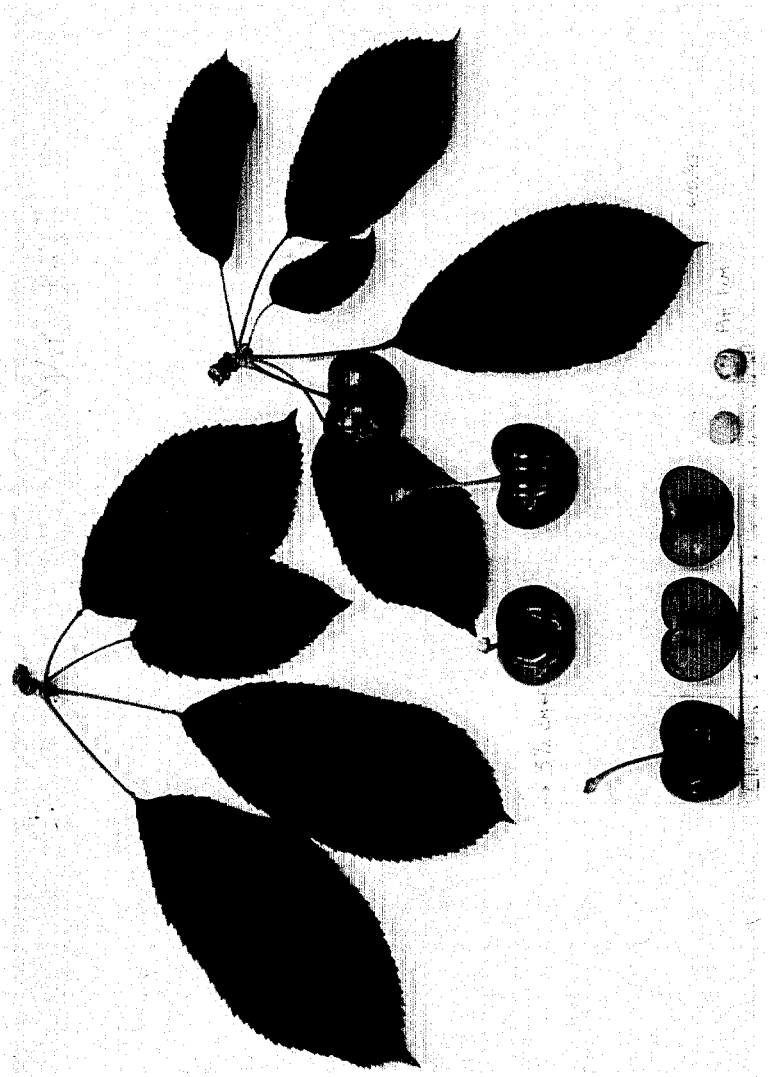

US00PP09723P

United States Patent [19]

Mancuso

[11] Patent Number: Plant 9,723

[45] Date of Patent: Dec. 3, 1996

[54] CHERRY TREE 'SCARLET'

[76] Inventor: Ciro Mancuso, 13448 Syacmore Ave., Patterson, Calif. 95363

[21] Appl. No.: 544,377

[22] Filed: Oct. 17, 1995

[51] Int. Cl.[6] ..... A01H 5/00

[52] U.S. Cl. ..... Plt./37

[58] Field of Search ..... Plt./37

*Primary Examiner*—James R. Feyrer

*Attorney, Agent, or Firm*—Townsend & Townsend & Crew

[57] ABSTRACT

The new variety of cherry tree, named 'Scarlet' blooms six days ahead of 'Van' and eight days ahead of 'Bing' and produces fruit uniformly very large, very firmed textured, with excellent flavor, exceptionally resistant to cracking and resilient to damage by wind and hail. The fruit matures evenly and exhibits mature qualities at an unusually early age. The fruit is short stemmed and has exceptional eating quality.

1 Drawing Sheet

DESCRIPTION

This invention relates to a new variety of sweet cherry tree "*Prunus avim* (L.) L.", found as a chance seedling growing among cultivated trees of the 'Van,' 'Bing,' 'Royal Anne,' and 'Tartarian' varieties in the inventor's orchard near Patterson, Stanislaus County, Calif. in 1975.

The seedling labeled, '7506B', was transplanted in January 1976 into an experimental row of seedlings for the purpose of tracking its fruiting characteristics. The tree first fruited in May of 1982. At that time, the unusual and desirable characteristics of the fruit were first observed. Scions of the seedling were grafted onto five trees of 'Mahaleb' rootstock in January of 1983 in a block of land owned by the inventor adjacent to the block where seedling '7506B' was first discovered. The grafted trees first produced fruit in 1988 and confirmed the fruit quality that was exhibited by the original seedling '7506B'.

In 1990, a five acre block of seedling trees were planted and budded with Scion wood from the five trees planted in 1983. That block of trees, now named 'Scarlet', reliably reproduced the fruit first observed by the original seedling '7506B'.

IN THE DRAWING

FIG. 1 illustrates leaves fruit and seeds typical of the new variety. Fruit is shown in top plan and side elevational views with stems. Fruit size is indicated and fruit interior is shown.

'Scarlet' exhibits very mature qualities at an unusually early age and tends to bear fruit regularly in large quantities with a lowered chilling requirement than any other commercial variety presently known to the inventor. 'Scarlet' blooms approximately six days ahead of 'Van' and eight days ahead of 'Bing' in the orchard of the inventor. The fruit is uniformly very large, short stemmed, very firm textured, and has excellent flavor. The external appearance of the fruit is glossy, shiny, and red/purple in color over the total area of the fruit. Flesh is varied in color in its different stages of ripening from white to red to deep purple.

During the maturation process, the fruit is exceptionally resistant to cracking and resilient to damage by wind and hail. Under normal and consistent weather conditions, the fruit matures evenly. The characteristics of 'Scarlet' make it a candidate for selection for wide scale commercial growing.

The heat tolerance of the tree and firmness of the fruit, with its relatively short thick stem, and resistance to suture, spurs and doubling make it well suited to the conditions of the west side and southern areas of the San Joaquin Valley which experience prolonged heat, both day and night, as well as windy conditions and are noted for inferior quality production of presently known cherry tree varieties.

'Scarlet' allows for the production of high quality firm, early cherries in areas noted for inferior quality production of presently known cherry tree varieties because of resistance of the variety to suture, spurs, and doubling.

It is anticipated that 'Scarlet' will require a lower ratio of pollinizers than normally recommended for similar varieties. 'Scarlet' is best pollinized by 'Tulare'. 'Scarlet' necessitates severe pruning to minimize fruit quantity and to obtain fruit of larger size.

SPECIFIC DESCRIPTION

The following specific description is of plant material grown on the inventor's orchard in Patterson, Calif. The fruit is described at firm maturity. Color definitions are from The Royal Horticultural Society Colour Chart.

Tree: Upright, medium size and vigor, vase formed, hardy for normal climatic conditions found in the San Joaquin Valley of Central California, very productive.

*Trunk.*—Average in diameter, medium surface texture, bark, grey brown (199 A).

*Branches.*—Medium in caliber, smooth surface texture, more reddish in color than 'Bing', greyed-orange (165 A).

*Leaves.*—Large, oval, abruptly tapering to an acute point, moderately coarse and serrated. Glands, one-two per leaf at base of leaf. Color, yellow-green (147-A).

*Stipules.*—Large, two in number at base of petiole.

*Leaf petiole.*—Long average, 4 cm in length.

Bloom:

Approximately 1½ cm larger than 'Bing', four to five blossoms per bud, petals, medium to large, white (155-C), bloom time, six days ahead of 'Van' or 'Bing', approximately March 12.

Fruit Uniformly very large—3.5 cm.

*Stem*—Short and thick.

*Fruit.*—Firm textured.

*Fruit form.*—Resembles 'Brooks,' U.S. Plant Pat. No. 6,676.

*Skin and flesh.*—Very firm and smooth and of average thickness. Skin color, at maturity, is red purple (59-A). Flesh color varies in stages of ripening from white (155-C) to red (57-A) to red purple (60-A).

*Ripening and date of maturity.*—Ripens evely, first pick is May 5, second pick May 11, approximately 6 days ahead of 'Van' and 'Bing.'

*Fruit flavor.*—Sweet, well balanced, rich flavor, well above average, especially for early season and maturity.

Stone:

*Size.*—1 cm, firmly attached and clings to fruit, round in form but slightly elongated, fairly flat based.

*Color.*—Greyed orange (177-C).

*Hilum.*—Ring showing circumference of stem attachment.

*Apex.*—Blunt.

*Surface.*—Smooth with ventral edge having slight single ridge and dorsal edge having predominant triple edge — no tendency to split.

Fruit use: Fresh market and for local and long distance shipping. Keeping quality is good, based on limited testing.

Insects and diseases:

No particular susceptibilities noted.

I claim:

1. I claim the new and distinct variety of cherry tree having the characteristics described and illustrated herein.

* * * * *